United States Patent [19]
Horng

[11] Patent Number: 5,498,397
[45] Date of Patent: Mar. 12, 1996

[54] AIR FRESHENER

[76] Inventor: Chin-Fu Horng, #30 Lane 161, Hua Cheng Rd., Hsin Chuaing City, Taipei Shien, Taiwan

[21] Appl. No.: 437,663

[22] Filed: May 9, 1995

[51] Int. Cl.$^6$ .................................................. A61L 9/12
[52] U.S. Cl. ....................... 422/124; 422/123; 422/305; 422/306
[58] Field of Search ..................... 422/4, 5, 123, 422/124, 305, 306; 239/34, 57, 60

[56] References Cited

U.S. PATENT DOCUMENTS

| | | | |
|---|---|---|---|
| 3,990,848 | 11/1976 | Corris | 422/4 |
| 3,993,444 | 11/1976 | Brown | 422/124 |
| 4,111,655 | 9/1978 | Quincey | 422/124 |
| 5,147,582 | 9/1992 | Holzner, Sr. et al. | 239/60 |
| 5,376,338 | 12/1994 | Zlotnik | 422/5 |

*Primary Examiner*—Robert J. Warden
*Assistant Examiner*—Theresa T. Snider
*Attorney, Agent, or Firm*—Morton J. Rosenberg; David I. Klein

[57] ABSTRACT

An air freshener is provided. The air freshener includes a base, a battery power supply and a fan motor mounted on the base and is covered by a motor cover. The fan motor has a fan blade extending above the motor cover. A shell covers the motor cover and the fan blade. The shell has a perforated open chamber in an upper portion thereof to hold spices. A transparent shade with air vents covers the open chamber. A power switch is provided and mounted on the shell. The power switch is connected in series between the battery power supply and the fan motor for controlling the operation of the fan motor, the fan motor producing currents of air for carrying the smell of the spices out of the transparent shade into the air through the air vents of the transparent shade.

3 Claims, 6 Drawing Sheets

AIR FRESHENER

BACKGROUND OF THE INVENTION

The present invention relates to air fresheners. More particularly, the present invention relates to an air freshener which uses a fan motor to produce currents of air for carrying the smell of the spices out of the housing of the air freshener for freshening the air.

Commercially available air fresheners commonly use a container to carry a liquid chemical or solid spices, permitting the smell of the liquid chemical or solid spices to be released into the air for freshening the room, motor vehicle, etc. When a liquid chemical is used for releasing a smell for freshening the air, it will be splashed over the surrounding area when the container is shaken heavily.

SUMMARY OF THE INVENTION

It is one object of the present invention to provide an air freshener which uses solid substances such as dehydrated flowers, solid spices, etc., for releasing a good smell for freshening the air. It is another object of the present invention to provide an air freshener which uses a fan motor to produce currents of air for carrying the smell of the dehydrated flowers, solid spices, etc., into the air.

According to one aspect of the present invention, the air freshener comprises a base, a battery power supply and a fan motor mounted on the base and covered by a motor cover. The fan motor has a fan blade extending above the motor cover. A shell covers the motor cover and fan blade. The shell has a perforated top open chamber to hold spices. A transparent shade with air vents covers the top open chamber. A power switch is mounted on the shell and is connected in series between the battery power supply and the fan motor for controlling the operation of the fan motor, causing the fan motor to produce currents of air for carrying the smell of the spices out of the transparent shade into the air through the air vents on the transparent shade. According to another aspect of the present invention, an AC-to-DC adapter may be installed so that battery power supply as well as city power supply can be used for driving the fan motor.

DETAILED DESCRIPTION OF THE PREFERRED EMBODIMENTS

Figure 1:
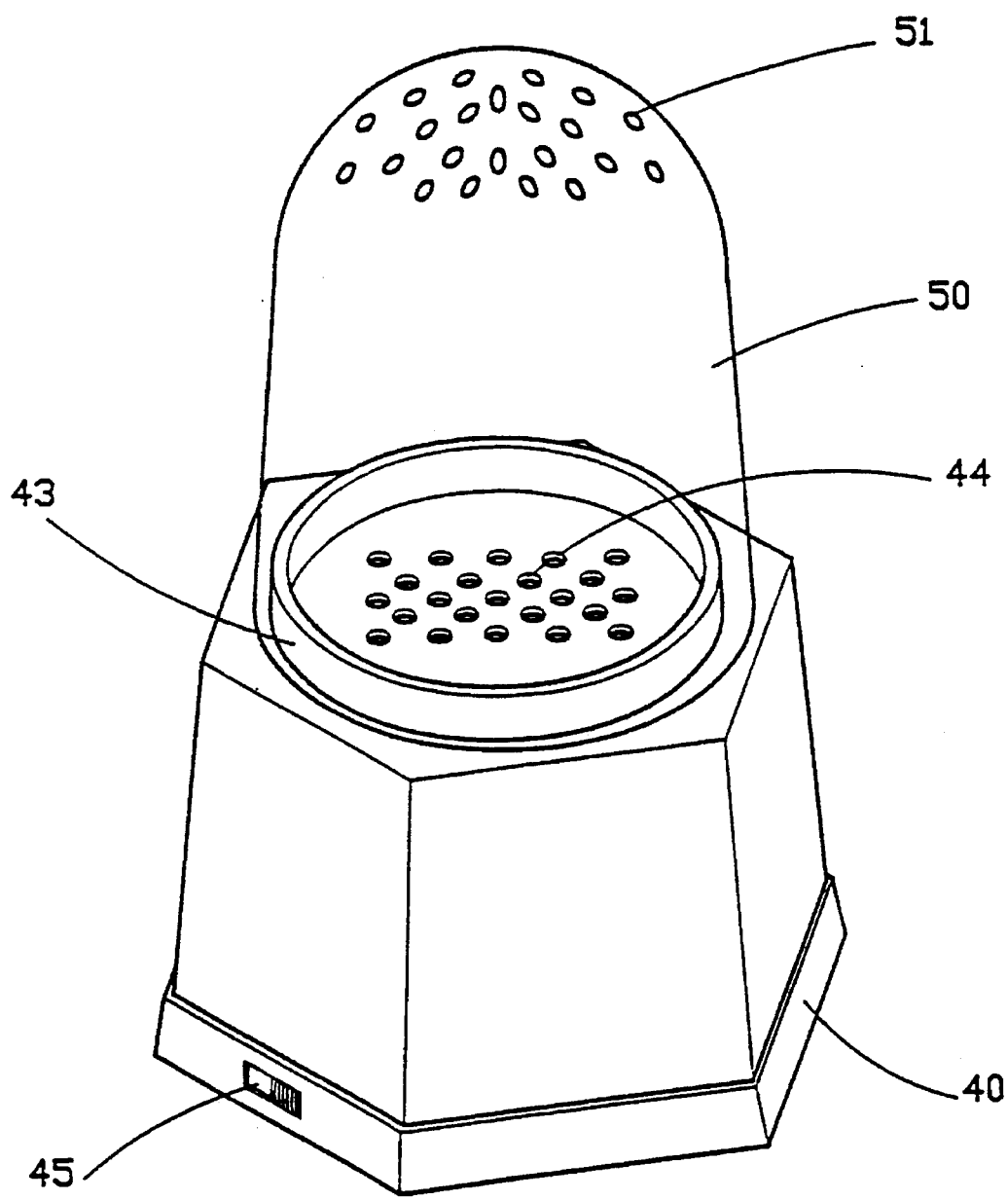
FIG. 1 is an elevational view of an air freshener according to the present invention.
Figure 2:
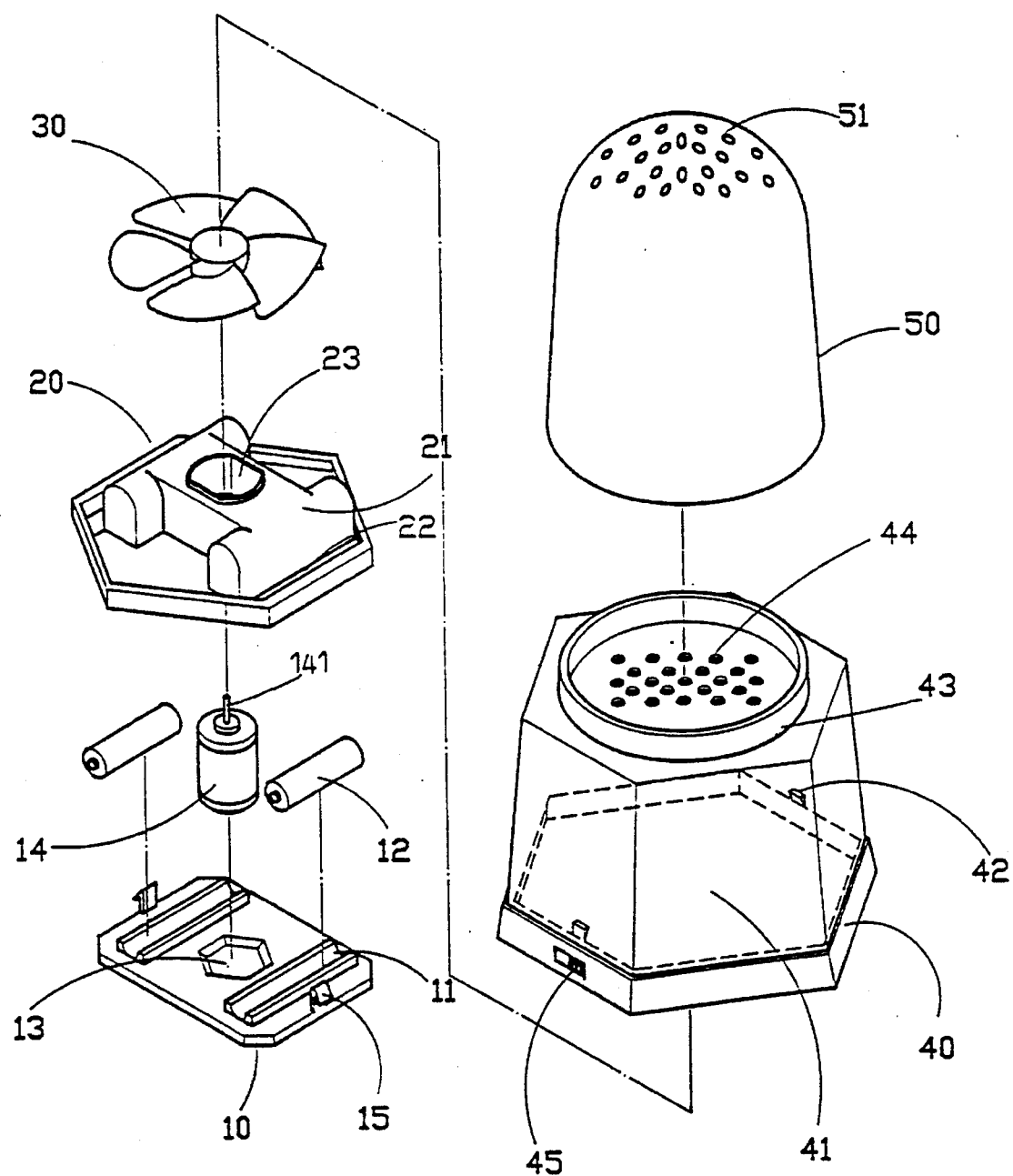
FIG. 2 is an exploded view of the air freshener shown in FIG. 1.
Figure 3:
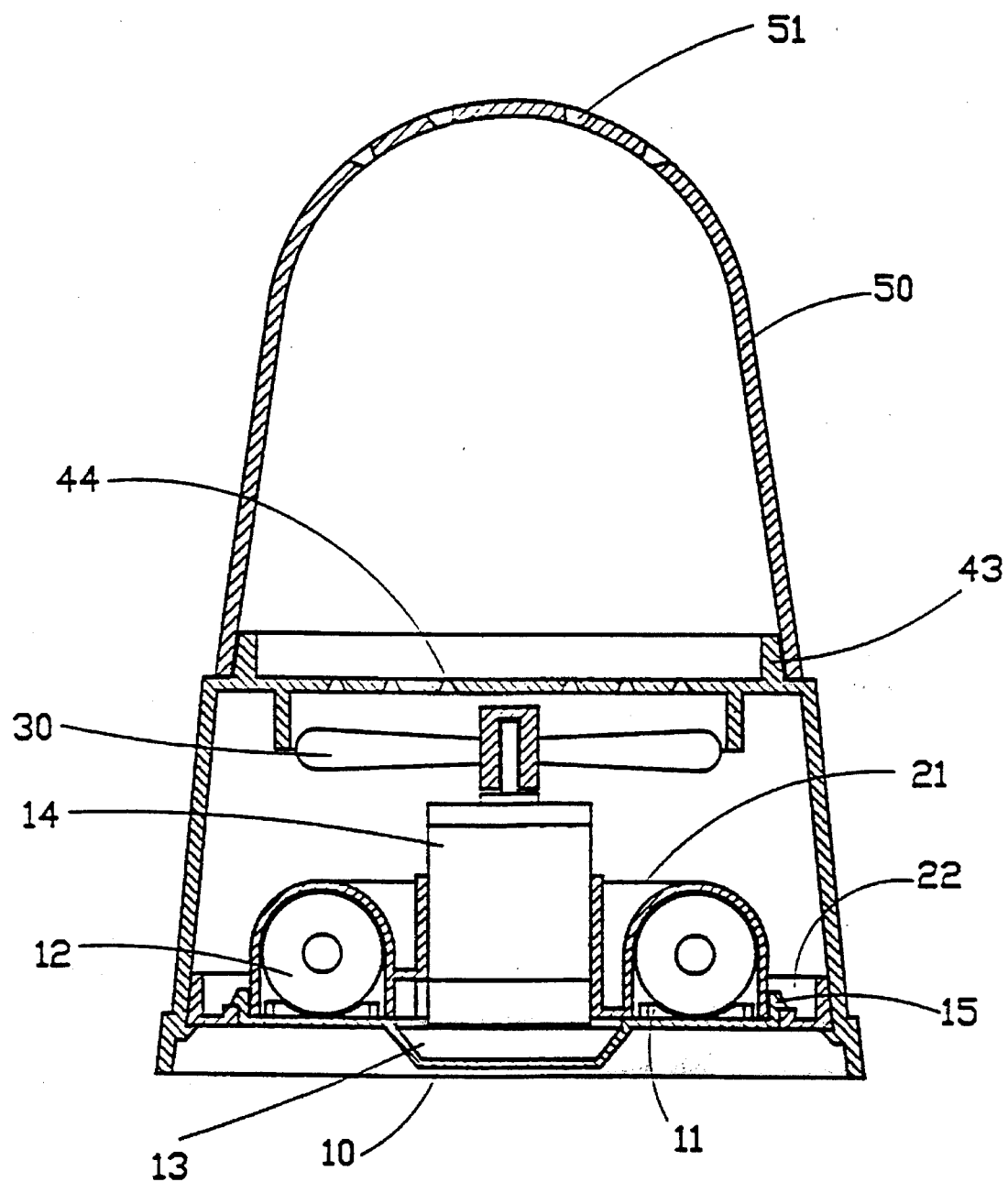
FIG. 3 is a side view in section of the air freshener shown in FIG. 1.
Figure 4:
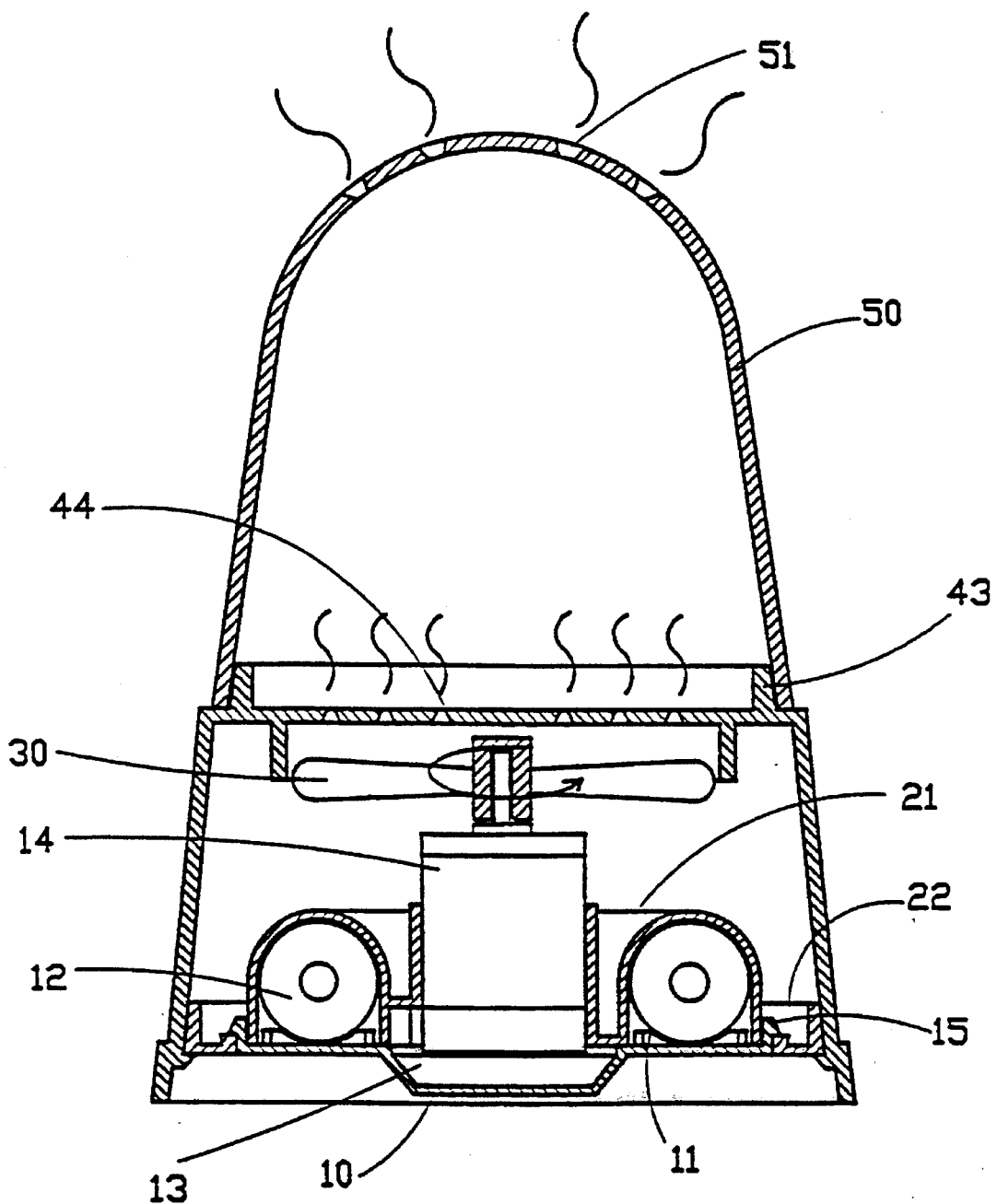
FIG. 4 is similar to FIG. 3 but showing the motor operated.

Referring to FIGS. 1–4, the base plate, referenced by 10, comprises two symmetrical battery chambers 11, a center recess 13, and two hooks 15 at two opposite sides. Two battery cells 12 are respectively mounted in the battery chambers 11 and connected in series. A motor 14 is mounted in the center recess 13. A motor cover 20 is fastened to the hooks 15 on the base plate 10 and covers the battery cells 12 and the motor 14. The motor cover 20 comprises a chamber 21 overlaying the battery chambers 11, two retaining holes 22 respectively fastened to the hooks 15 of the base plate 10, and a center motor mounting hole 23, which receives the motor 14. A fan blade 30 is coupled to the output shaft 141 of the motor 14 outside the motor cover 20. A shell 40 covers the fan blade 30 and the motor cover 20. The shell 40 comprises a bottom chamber 41, which receives the base plate 10 and the motor cover 20. Two opposing retainer rods 42 fasten to the motor cover 20 to hold the motor cover 20 inside the bottom chamber 41. Shell 40 also includes a top circular open chamber 43 with a plurality of air vents 44 formed therein and in communication with the bottom chamber 41. A power switch 45 is connected in series between the battery cells 12 and the motor 14 for controlling the operation of the motor 14. A transparent shade 50 is fastened to the shell 40 and covers the top open chamber 43. The shade 60 has a plurality of air vents 51 on the smoothly curved top side thereof.

Figure 5:
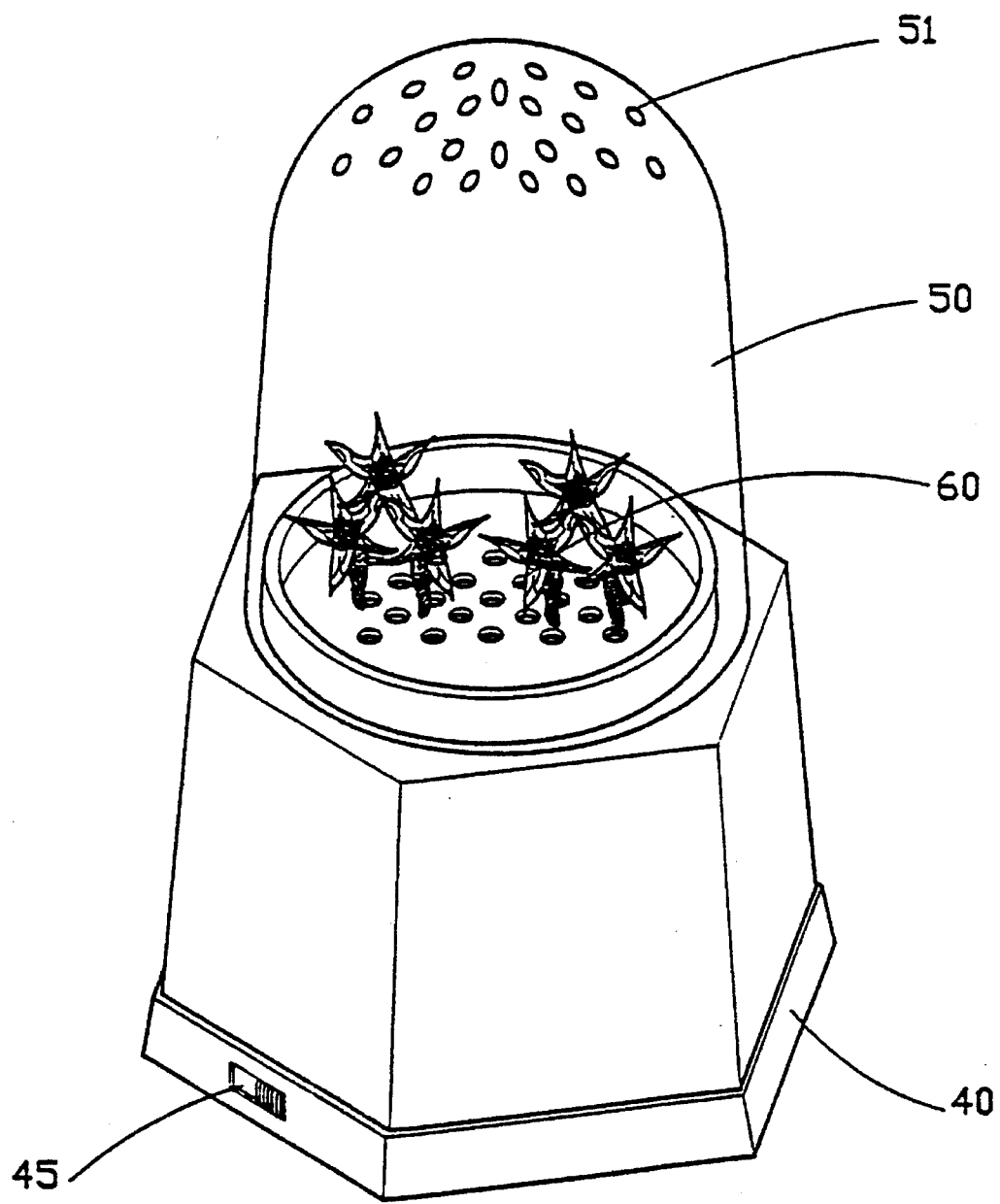
FIG. 5 is an applied view of the present invention, showing dehydrated flowers placed in the top open chamber of the shell of the air freshener.

Referring to FIG. 5, dehydrated flowers or spices 60 are put in the top open chamber 43 and covered within the transparent shade 50. When the power switch is switched on, the smell of the dehydrated flowers or spices 60 is carried out of the transparent shade 50 into the air through the air vents 51 by the currents of air induced by the fan blade 30.

Figure 6:
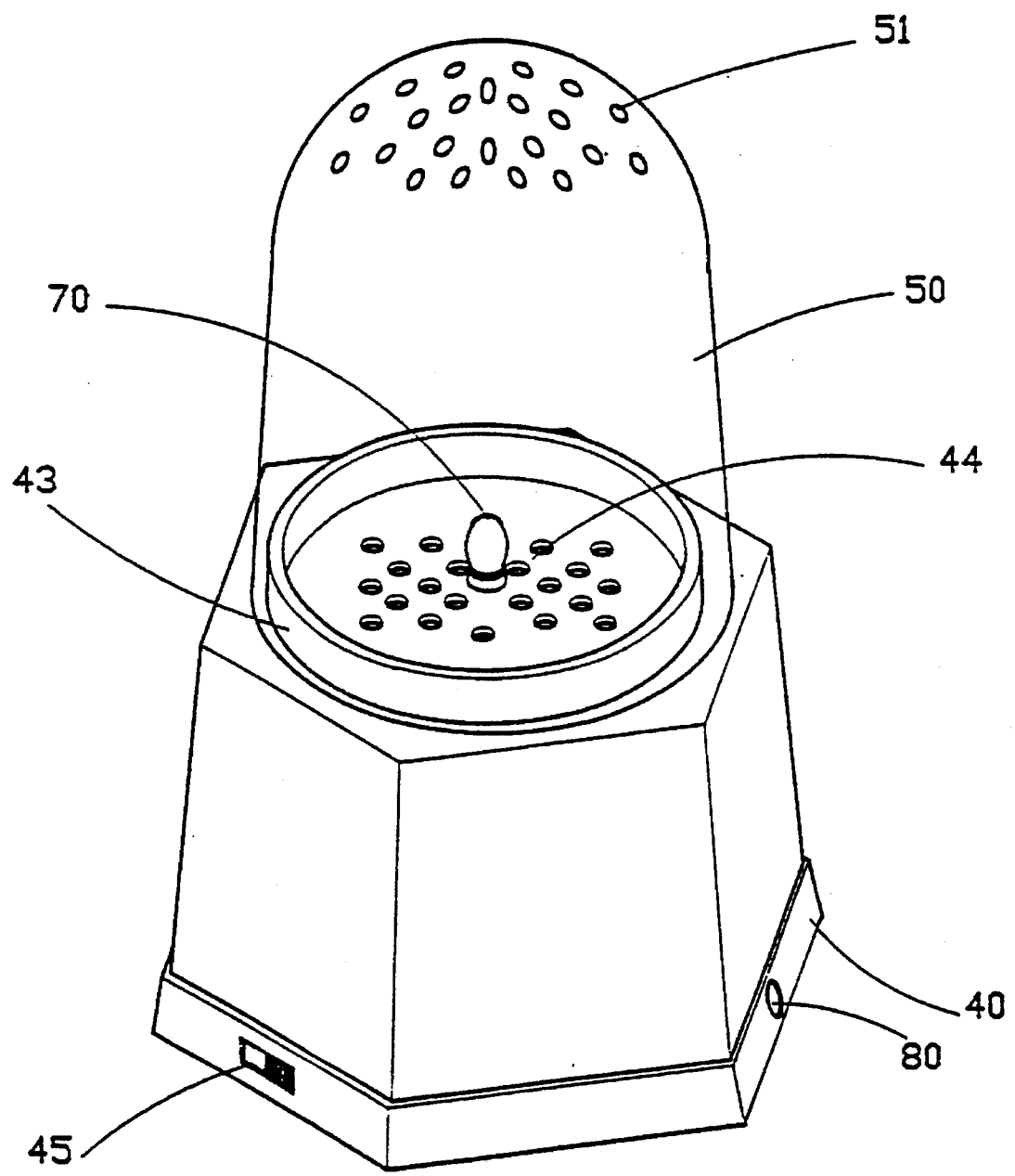
FIG. 6 is another applied view of the present invention, showing a lamp bulb and an AC-to-DC adapter installed in the shell of the air freshener.

FIG. 6 shows an alternate form of the present invention, in which a lamp bulb 70 is installed in the top open chamber 43 of the shell 40. An AC-to-DC adapter 80 is mounted to the shell 40 for converting AC to DC for the motor 14.

It is to be understood that the drawings are designed for purposes of illustration only, and are not intended as a definition of the limits and scope of the invention disclosed.

I claim:

1. An air freshener, comprising:

a base, said base including a pair of symmetrical battery chambers, said base having a centrally disposed recess formed between said pair of battery chambers and a pair of hooks disposed on opposing sides thereof;

a pair of battery cells respectively mounted within said pair of battery chambers;

a motor cover covering said base and secured thereto by said pair of hooks, said motor cover having a motor mounting hole formed therethrough;

a fan motor mounted within said centrally disposed recess of said base and disposed within said motor mounting hole of said motor cover, said fan motor having an output shaft extending from said motor cover through said motor mounting hole;

a fan blade coupled to said output shaft external said motor cover;

a shell over laying and coupled to said motor cover, said shell having a bottom chamber for receiving said combined base, motor cover, fan motor and fan blade, said shell having an open top chamber for holding spices therein, said open top chamber having a bottom wall with a plurality of air vents formed therethrough and in open communication with said bottom chamber;

a transparent shade having an open bottom end covering said open top chamber of said shell and the spices therein, said transparent shade having a closed upper end with a plurality of through openings formed therein; and, a power switch mounted on said shell and electrically coupled in series relation between said battery cells and said fan motor for controlling operation of said fan motor, whereby operation of said fan motor causes said fan blade to produce air currents through said plurality of air vents for carrying an aroma of the spices from said plurality of through openings of said transparent shade.

2. The air freshener of claim 1 further comprising a lamp bulb mounted in said open top chamber of said shell and connected to said battery cells through said power switch.

3. The air freshener of claim 1 further comprising an AC-to-DC adapter mounted on said shell to convert AC to DC for said fan motor.

* * * * *